US008409532B2

(12) United States Patent
Teng et al.

(10) Patent No.: US 8,409,532 B2
(45) Date of Patent: Apr. 2, 2013

(54) APPARATUS FOR INSULATED ISOTHERMAL POLYMERASE CHAIN REACTION

(75) Inventors: Ping-Hua Teng, Taichung (TW); Cheng Su, Taichung (TW)

(73) Assignee: Genereach Biotechnology Corp., Taichung (TW)

( * ) Notice: Subject to any disclaimer, the term of this patent is extended or adjusted under 35 U.S.C. 154(b) by 0 days.

(21) Appl. No.: 13/323,121

(22) Filed: Dec. 12, 2011

(65) Prior Publication Data

US 2012/0244047 A1 Sep. 27, 2012

(30) Foreign Application Priority Data

Mar. 22, 2011 (TW) ............................ 100109782 A

(51) Int. Cl.
*B01L 9/06* (2006.01)
*C12M 1/34* (2006.01)
*C12M 3/00* (2006.01)
*C12M 1/00* (2006.01)

(52) U.S. Cl. .................. 422/562; 435/287.2; 435/288.7; 435/303.1

(58) Field of Classification Search ........................ None
See application file for complete search history.

(56) References Cited

U.S. PATENT DOCUMENTS 5,038,852 A * 8/1991 Johnson et al. ............... 165/267
5,281,516 A * 1/1994 Stapleton et al. ................ 435/3
5,616,301 A * 4/1997 Moser et al. .................... 422/64
5,935,524 A * 8/1999 Bass et al. ...................... 422/562
6,403,037 B1 * 6/2002 Chang et al. ................. 422/68.1
6,472,186 B1 * 10/2002 Quintanar et al. ........... 435/91.2
7,133,726 B1 * 11/2006 Atwood et al. ................... 700/1
7,255,833 B2 * 8/2007 Chang et al. .................. 422/417

* cited by examiner

*Primary Examiner* — Jill Warden
*Assistant Examiner* — Brittany Fisher
(74) *Attorney, Agent, or Firm* — Muncy, Geissler, Olds & Lowe, PLLC

(57) ABSTRACT

An apparatus for holding a test tube in which insulated isothermal polymerase chain reaction is performed includes a heat insulating mount and a heating member. The heat insulating mount has a main body provided with a receiving space for receiving a bottom of the test tube, a lateral channel communicated between the receiving space and an ambient environment, and an upper channel communicated between the receiving space and the ambient environment for insertion of the test tube. The heating member is inserted into the lateral channel for stopping at the bottom of the test tube. The apparatus can minimize the influence caused by the high temperature generated from the heat source on the heat dissipation of the reaction mixture in middle and upper sections of the test tube. The apparatus is suitable for the fluorescent detection of PCR reaction.

11 Claims, 4 Drawing Sheets

APPARATUS FOR INSULATED ISOTHERMAL POLYMERASE CHAIN REACTION

BACKGROUND OF THE INVENTION

1. Field of the Invention

The present invention relates generally to apparatuses for use in polymerase chain reaction (hereinafter referred to as "PCR") and more particularly, to an apparatus for performing insulated isothermal PCR.

2. Description of the Related Art

In the filed of biotechnology, polymerase chain reaction (PCR) is a well-known technology used to amplify specific nucleic acid sequences. The PCR process comprises three major steps including denaturation, primer annealing and extension, which require different reaction temperatures. The required temperature for the denaturation step is typically in a range between 90° C. and 97° C. The required temperature for the primer annealing step will depend on the melting temperature of the primer used. Typically, the annealing temperature ranges from 35° C. to 65° C. The required temperature for the extension step is typically about 72° C.

The convective PCR is generally performed by immersing the bottom of a test tube which contains a reaction mixture into a hot water in such a way that the rest portion of the test tube is exposed to atmosphere at room temperature for heat dissipation. As a result, the temperature of the reaction mixture will gradually decrease from the bottom of the reaction mixture having a temperature of about 97° C. toward the liquid level of the reaction mixture having a temperature of about 35° C. Because of the temperature gradient, the heat convection is induced, such that the reaction mixture will flow through various regions having different temperatures and then undergo different reaction steps.

In the conventional convective PCR apparatus, high-temperature vapor generated above the surface of the hot water will convectively flow upwardly and then affect the heat dissipation around the middle and upper sections of the test tube, resulting in that the temperature at the level of the reaction mixture may not be lowered enough to the required temperature for conducting the primer annealing step. In addition, fluorescence is commonly used to detect the completion of PCR reaction. That is, a fluorescent dye is added into the reaction mixture and a laser ray is used to stream through the bottom of the test tube to the reaction mixture to detect the intensity of the fluorescence light. In the conventional apparatus for convective PCR, since the bottom of the test tube is immersed in the hot water for being heated, the hot water will badly affect the laser ray, making fluorescent detection impossible.

SUMMARY OF THE INVENTION

The present invention has been accomplished in view of the above-noted circumstances. It is the primary objective of the present invention to provide an apparatus for insulated isothermal PCR, which can minimize the influence, which is caused by hot air generated from the heat source, on the heat dissipation of middle and upper sections of the test tube.

Another objective of the present invention is to provide an apparatus for insulated isothermal PCR, which is suitable for fluorescent detection of PCR reaction.

To achieve the above-mentioned objectives, the apparatus provided by the present invention is adapted for holding a test tube in which insulated isothermal polymerase chain reaction is performed, which comprises a heat insulating mount and a heating member. The heat insulating mount has a main body provided with a receiving space for receiving a bottom of the test tube, a lateral channel communicated between the receiving space and an ambient environment, and an upper channel communicated between the receiving space and the ambient environment for insertion of the test tube. The heating member is inserted into the lateral channel for stopping at the bottom of the test tube. By this way, the influence caused by hot air generated from the heat source on the heat dissipation of the middle and upper sections of the test tube can be reduced and the apparatus of the present invention is suitable for fluorescent detection of PCR reaction.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
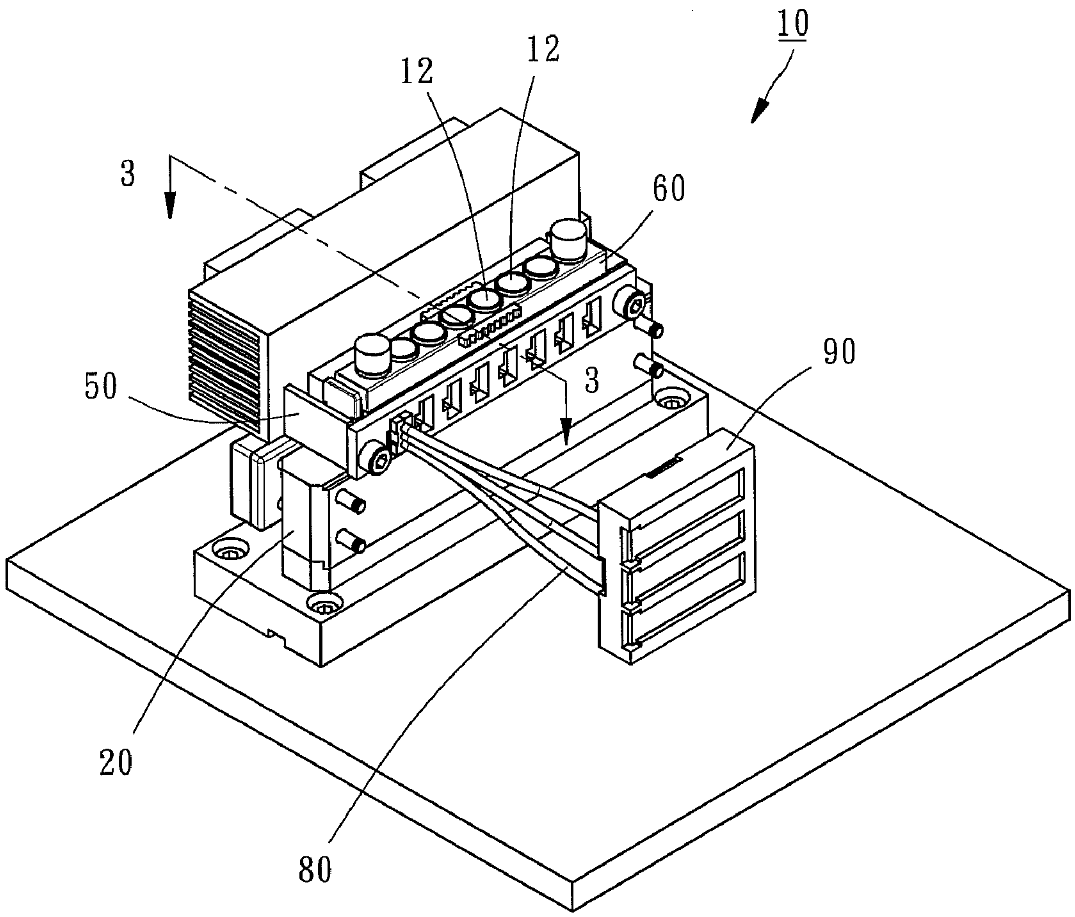
FIG. 1 is a perspective view of an apparatus for insulated isothermal PCR according to a preferred embodiment of the present invention.
Figure 2:
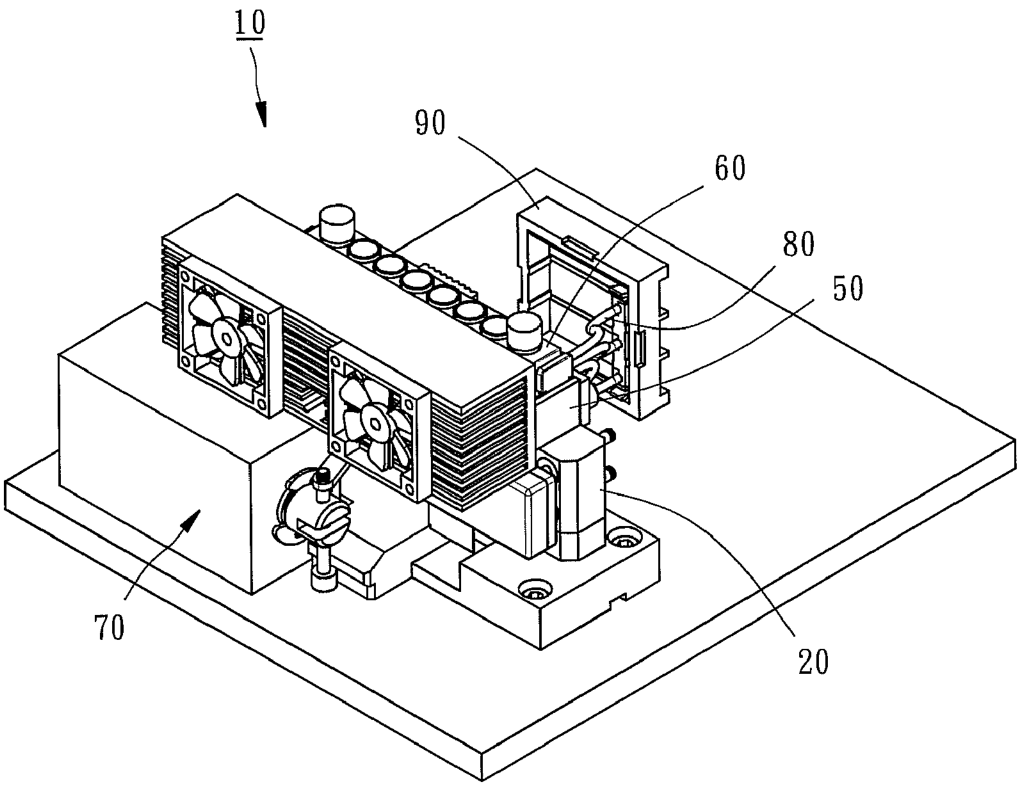
FIG. 2 is another perspective view of the apparatus for insulated isothermal PCR according to the preferred embodiment of the present invention.
Figure 3:
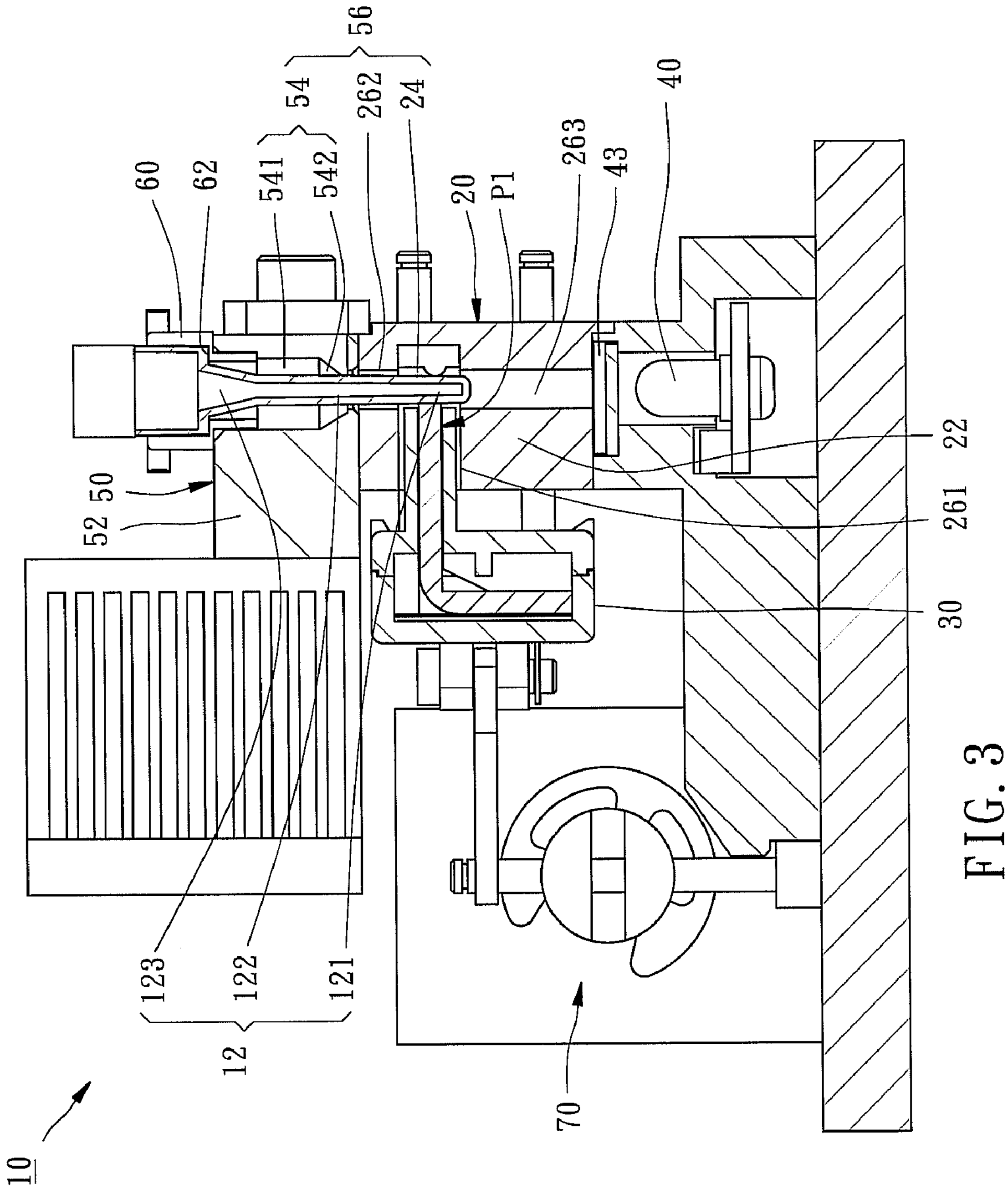
FIG. 3 is a cross-sectional view taken along line 3-3 of FIG. 1.

As shown in FIGS. 1-3, an apparatus 10 for insulated isothermal PCR, which is provided according to a preferred embodiment of the present invention, mainly comprises a heat insulating mount 20, a heating member 30, a light unit 40, a heat dissipating mount 50, a tube rack 60 and a drive 70.

The insulating mount 20 includes a main body 22 provided at an inside thereof with a receiving space 24 for receiving a bottom 121 of a test tube 12, a lateral channel 261 communicated with the receiving space 24 to an ambient environment, and an upper channel 262 communicated with the receiving space 24 to the ambient environment for insertion of the test tube 12. The heating member 30 has an end portion inserted into the lateral channel 261 of the heat insulating mount 22 for stopping at the bottom 121 of the test tube 12.

The heat insulating mount 20 is made from a plastic material or a ceramic material. For the plastic material, nylon-glass fiber composite or acrylic-ABS (Acrylonitrile Butadiene Styrene) composite having a low thermal conductivity can be used. The heating member 30 is made of metal, such as copper; therefore, the heating member 30 has a high thermal conductivity. The heating member 30 adopts electricity to generate heat energy, thereby preventing the generation of the high-temperature vapor. In addition, the gap between the upper channel 262 and the test tube 12 is small; therefore, even if the heating member 30 heats the air within the receiving space 24, the heated air will have minor influence on the heat dissipation of the middle and upper sections 122 and 123 of the test tube 12.

In order to detect the resultant of reaction in every cycling of the PCR, i.e. in order to perform the so-called fluorescent detection of PCR, the light unit 40 provided by the preferred embodiment of the present invention is arranged below the heat insulating mount 20, as shown in FIG. 3. In addition, the heat insulating mount 20 is further provided with a lower channel 263 for enabling entrance of the light emitted from the light unit 40 into the receiving space 24. The light having a specific wavelength and emitted by the light unit 40 will stream through the lower channel 263 to the PCR mixture contained in the test tube 12 to induce the particles having fluorescence characteristic in the PCR mixture to emit fluorescent light. By means of using an optical fiber 80 and a photo-sensing device 90 to detect the intensity of the fluorescent light in the test tube 12, the resultant of reaction in the reaction mixture can be quantified.

Instead of using hot water, the present invention adopts the heating member 30 to heat the bottom 121 of the test tube 12; therefore, the light emitted from the light unit 40 will not be affected by hot water. In addition, because the heating member 30 is arranged at a lateral side of the test tube 12, the light unit 40 is able to be arranged below the test tube 12; therefore, the light emitted from the light unit 40 can stream on the whole test tube. In light of this, the apparatus 10 provided by the present invention is suitable for the fluorescent detection of PCR, thereby achieving the objectives of the present invention.

In practice, the light unit 40 can be realized by an LED module, a halogen lamp, a tritium lighting unit or a xenon arc lamp. In addition, a filter 43 can be arranged between the receiving space 24 and the light unit 40 to filter the light emitted from the light unit 40 for allowing the light having a specific wavelength to pass therethrough and stream on the test tube 12.

In order to enhance the heat dissipating effect at the middle and upper sections 122 and 123 of the test tube 12, the heat dissipating mount 50 is further provided in the preferred embodiment of the present invention. As shown in FIG. 3, the heat dissipating mount 50 includes a main body 52 provided with a through hole 54 penetrating therethrough. The main body 52 is mounted on the heat insulating mount 20 in such a way that the through hole 54 is in alignment with the upper channel 262 of the heat insulating mount 20 for insertion of the test tube 12. In PCR process, because the middle and upper sections 122 and 123 are located inside the through hole 54 of the heat dissipating mount 50 and the heat dissipating mount 50 is made of a metal material having a high heat transfer coefficient, such as aluminum alloy or copper alloy, the heat energy of the reaction mixture in the test tube 12 will be transferred through the air surrounding the test tube 12 to the heat dissipating mount 50 for further heat dissipation. As a result, when the reaction mixture convectively flows upwardly, the reaction mixture will gradually cool. Specifically speaking, when the reaction mixture flows to the middle section 122 of the test tube 12, the reaction mixture can be cooled to a temperature of about 72° C., which is the required temperature suitable for conducting the extension step. When the reaction mixture flows to the liquid level, the reaction mixture can be further cooled to a temperature of about 35° C., which is lower than the required temperature for conducting the primer annealing step. By this repeated cycling of convection flow, the polymerase chain reaction will continuously run.

In fact, the receiving space 24 of the heat insulating mount 20, the upper channel 262 of the heat insulating mount 20 and the through hole 54 of the heat dissipating mount 50 combinedly form a reaction chamber 56 and the heat energy in the reaction chamber 56 will be transferred to the ambient environment through the heat dissipating mount 50. In general, the heating member 30 introduces heat energy into the bottom 121 of the test tube 12, and the heat dissipating mount 50 transmits the heat energy at the middle and upper sections 122 and 123 of the test tube 12 and the heat energy from the hot air in the upper channel 262 of the heat insulating mount 20 to the ambient atmosphere, such that the reaction mixture in the test tube 20 that is held in the reaction chamber 56 and the ambient air surrounding the test tube 12 will have a temperature gradually and upwardly decreasing.

In other words, the heat insulating mount 20 prohibits heat exchange between the reaction chamber 56 and the ambient atmosphere, and the heat dissipating mount 50 dissipates the internal heat to the ambient atmosphere. As a result, the environment influence outside the reaction chamber 56 can be efficiently precluded, and a stable temperature gradient can be formed in the reaction chamber 56, such that the insulated isothermal polymerase chain reaction can be performed stably.

In order to establish a specific temperature gradient in the test tube 12 helpful for performing PCR, the through hole 54 of the heat dissipating mount 50 is provided with a relatively big diameter section 541 and a relatively small diameter section 542 located below the relatively big diameter section 541. In this way, the heat dissipation of the reaction mixture at the region corresponding to the relatively small diameter section 542 will be higher than that at the region corresponding to the relatively big diameter section 541. It is revealed by experiments that the configuration of the heat dissipating mount 50 provided by the present invention makes PCR more efficient. The aforesaid experiments for PCR were conducted in seven different environmental temperatures ranging from 10° C. to 40° C. with a condition that the temperature of the heating member 30 is set at a range of 104° C. to 115° C. for heating the reaction mixture inside the bottom 121 of the test tube 12 to a temperature of 93° C. to 97° C. The temperature of the heat dissipating mount 50 measured is in a range from 36° C. to 53° C., and the temperature at the reaction mixture level measured ranges from 36° C. to 53° C.; therefore, the PCR can be performed efficiently.

In order to stably mount the test tube 12 in the heat dissipating mount 50 and the heat insulating mount 20, a tube rack 60 can be further provided on the heat dissipating mount 50. The tube rack 60 is provided with a receiving hole 62 for insertion of the test tube 12. The receiving hole 62 has a shape complementary to the shape of the upper section 123 of the test tube 12, such that the test tube 12 can be stationarily set in the receiving hole 62 of the tube rack 60.

Figure 4:
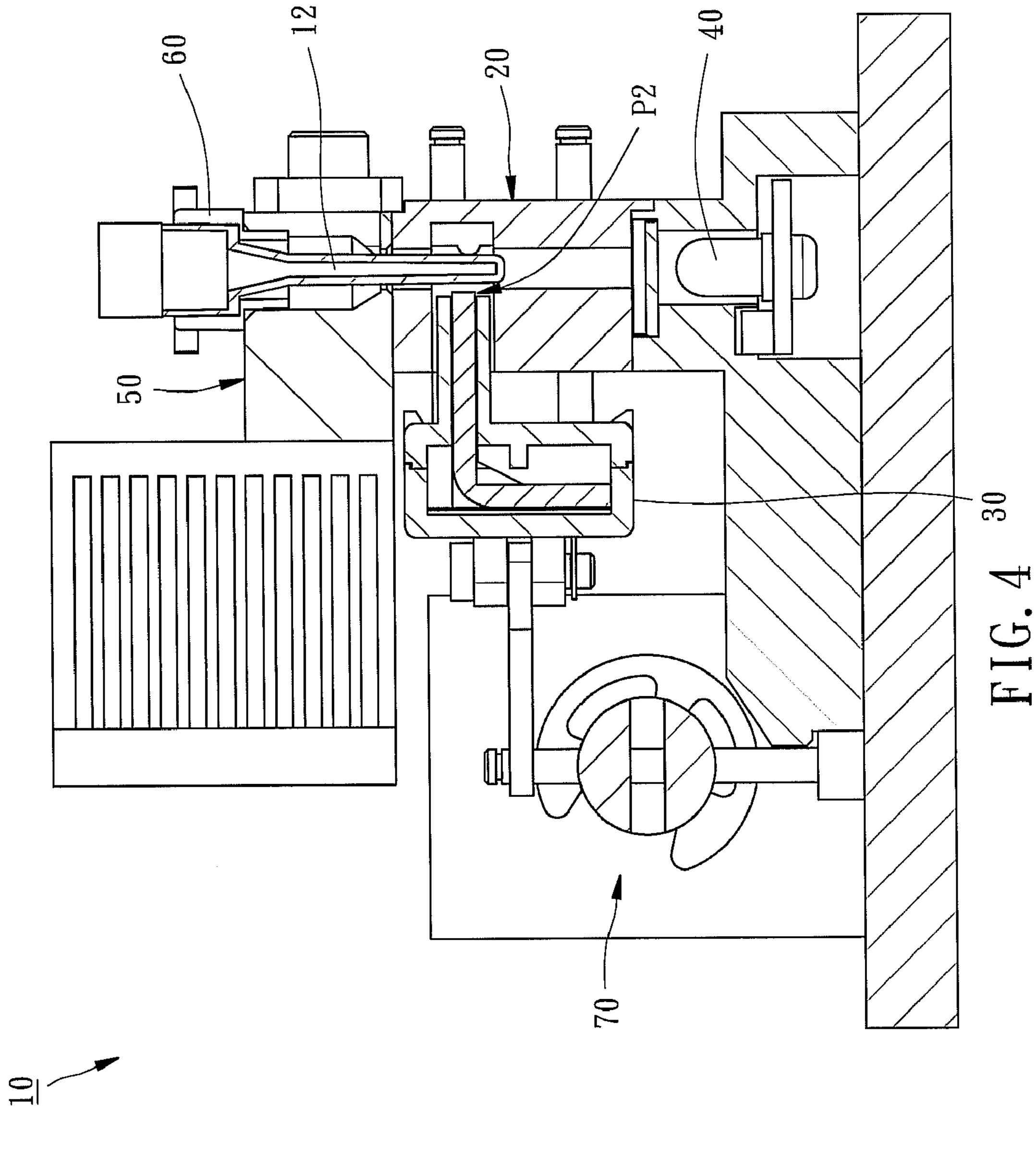
FIG. 4 is a schematic view showing the movement of the heating member.

Referring to FIGS. 3 and 4, a drive 70 can be further provided to be connected with the heating member 30 for driving the heating member 30 to move between a contact position P1 and a release position P2. For the drive 70, a motor, pneumatic cylinder or oil cylinder can be used. When the heating member 30 is driven by the drive 70 to move to the contact position P1, the heating member 30 contacts the bottom 121 of the test tube 12, such that the reaction mixture in the bottom 121 of the test tube 12 can be heated. When the heating member 30 is forced by the drive 70 to the release position P2, the heating member 30 moves away from the test tube 12 to stop heating the bottom 121 of the test tube 12.

The invention being thus described, it will be obvious that the same may be varied in many ways. For example, the LED module and the filter 43 can be installed in the lower channel 263 of the heat insulating mount 20 such that the apparatus 10 of the present invention can be compactly made. Further, a laser module can be used as the light unit 40, such that the filter 43 can be eliminated. Such variations are not to be regarded as a departure from the spirit and scope of the invention, and all such modifications as would be obvious to one skilled in the art are intended to be included within the scope of the following claims.

What is claimed is:

1. In combination, an apparatus for holding a test tube and the test tube having a bottom, a middle section and an upper section in which insulated isothermal polymerase chain reaction is performed, the apparatus comprising:

a heat insulating mount having a main body provided with a receiving space [for] receiving the bottom of the test tube, a lateral channel communicated between the receiving space and an ambient environment, and an upper channel communicated between the receiving space and the ambient environment for insertion of the test tube; and a heating member inserted into the lateral channel for stopping at and introducing heat energy into the bottom of the test tube; and a heat dissipating mount having a main body mounted on the heat insulating mount and provided with a through hole in communication with the upper channel of the heat insulating mount for insertion of the test tube, the upper and middle portion of the test tube received within the heat dissipating mount, the heat dissipating mount being adapted to transmit the heat energy at the middle and upper sections of the test tube to the ambient atmosphere while the heating member is introducing the heat energy into the bottom of the test tube.

2. The apparatus of claim 1, wherein the heat insulating mount is made from a plastic material or a ceramic material.

3. The apparatus of claim 1, wherein the heating member is made of metal.

4. The apparatus of claim 1, further comprising a light unit located below the heat insulating mount; wherein the heat insulating mount is provided with a lower channel through which the light emitted from the light unit enters into the receiving space.

5. The apparatus of claim 4, further comprising a filter arranged between the receiving space and the light unit; wherein the light unit is an LED module, a halogen lamp, a tritium lighting unit or a xenon arc lamp.

6. The apparatus of claim 4, wherein the light unit is a laser module.

7. The apparatus of claim 1, wherein the heat dissipating mount is made of metal.

8. The apparatus of claim 1, wherein the receiving space of the heat insulating mount, the upper channel of the heat insulating mount and the through hole of the heat dissipating mount combinedly form a reaction chamber and a heat energy in the reaction chamber is transferred to the ambient environment through the heat dissipating mount.

9. The apparatus of claim 1, wherein the through hole of the heat dissipating mount has a relatively big diameter section and a relatively small diameter section located below the relatively big diameter section.

10. The apparatus of claim 1, further comprising a tube rack mounted on the heat dissipating mount and provided with a receiving hole for insertion of the test tube.

11. The apparatus of claim 1, further comprising a drive connected with the heating member for moving the heating member between a contact position where the heating member contacts the bottom of the test tube and a release position where the heating member discontacts from the test tube.

* * * * *